United States Patent [19]
Gopakumaran et al.

[11] Patent Number: 5,842,998
[45] Date of Patent: *Dec. 1, 1998

[54] APPARATUS FOR DETERMINING THE CONDUCTIVITY OF BLOOD

[75] Inventors: Balakrishnan Gopakumaran, Cleveland, Ohio; Peter K. Osborn, West Allis, Wis.; John H. Petre, Cleveland Heights, Ohio

[73] Assignees: Cleveland Clinic Foundation, Cleveland, Ohio; Marquette Medical Systems, Milwaukee, Wis.

[ * ] Notice: The term of this patent shall not extend beyond the expiration date of Pat. No. 5,827,192.

[21] Appl. No.: 842,640

[22] Filed: Apr. 16, 1997

Related U.S. Application Data

[63] Continuation-in-part of Ser. No. 701,177, Aug. 21, 1996.

[51] Int. Cl.$^6$ ........................................................ A61B 5/02
[52] U.S. Cl. ............................................................. 600/547
[58] Field of Search .................................... 600/374, 381, 600/454, 481, 485–486, 506, 508, 510, 526, 547

[56] References Cited

U.S. PATENT DOCUMENTS

| | | | |
|---|---|---|---|
| 4,380,237 | 4/1983 | Newbower | 128/693 |
| 4,785,823 | 11/1988 | Eggers | 128/692 |
| 5,453,576 | 9/1995 | Krivitski | 128/668 |
| 5,595,183 | 1/1997 | Swanson et al. | 600/510 |

*Primary Examiner*—Jeffrey R. Jastrzab
*Assistant Examiner*—Ryan Carter
*Attorney, Agent, or Firm*—Michael Best & Friedrich LLP

[57] ABSTRACT

An in vivo apparatus for determining the absolute conductivity of a liquid such as human blood, including the steps of determining a location in a ventricle of a patient's heart at which blood conductivity may be measured effectively, positioning a catheter having a plurality of spaced electrodes in the ventricle such that at least a pair of adjacent electrodes are positioned at the location, applying a current of known magnitude to the adjacent electrodes, measuring the voltage between the adjacent electrodes, and determining the conductivity of the patient's blood from the known current and measured voltage.

7 Claims, 1 Drawing Sheet

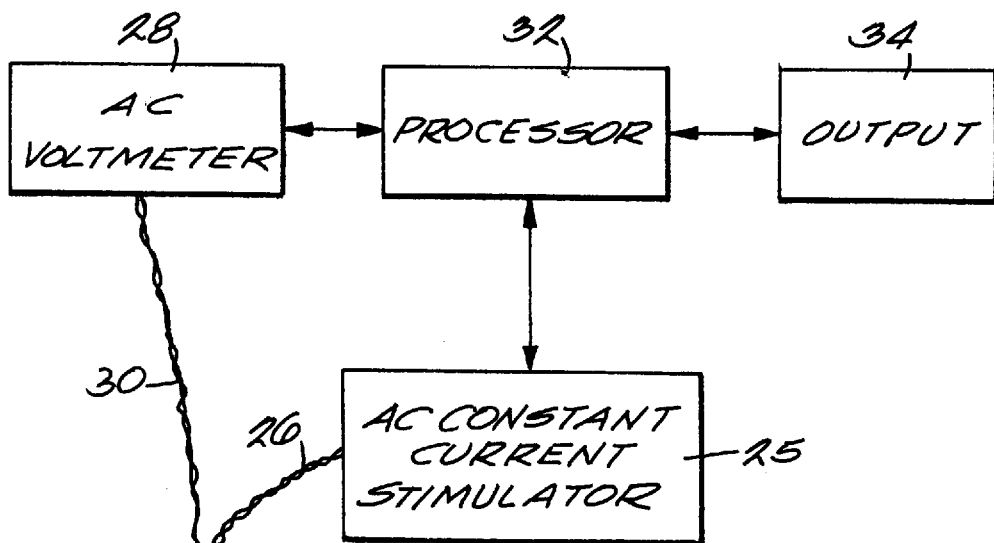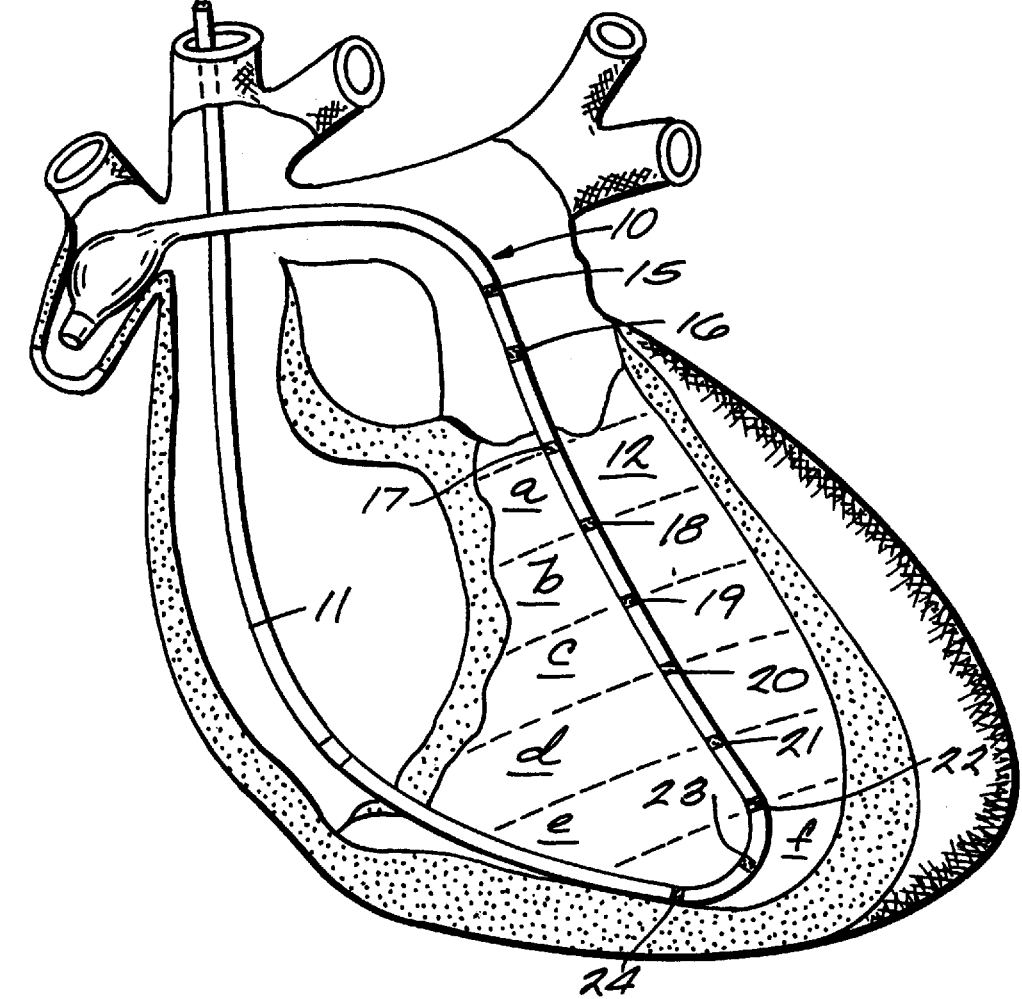

APPARATUS FOR DETERMINING THE CONDUCTIVITY OF BLOOD

CROSS REFERENCE TO RELATED APPLICATION

This is a continuation-in-part of application Ser. No. 08/701,177 filed Aug. 21, 1996, still pending.

BACKGROUND OF THE INVENTION

This invention relates to cardiac monitoring and more particularly to an apparatus for determining the absolute electrical conductivity of blood.

One of the parameters routinely monitored in heart patients is cardiac output which is generally measured in liters per minute and corresponds to the heart's stroke volume multiplied by the heart rate. Cardiac output is particularly significant during surgery as an indication of heart performance and the adequacy of blood circulation.

There are several known methods of measuring cardiac output including thermal dilution, contrast angiography and the conductance catheter method. Of these, the conductance catheter method can potentially measure the absolute ventricular volume continuously in real time and involves positioning a multi-electrode catheter in the patient's right ventricle. A constant electric current having a fixed frequency is applied to spaced apart drive electrodes. Signals at pairs of electrodes disposed between the drive electrodes are sampled. The volume can then be computed using one of several expressions, such as for example:

$$\text{Volume} = Ih^2/Vs$$

Where:  $I$ = the known constant current source
$h$ = the distance between sampled electrodes; and
$V$ = the voltage between sampled pair of electrodes
$s$ = conductivity of the medium;

Conductance catheter methods of cardiac output measuring are disclosed in U.S. Pat. Nos. 4,674,518; 4,721,115; 4,898,176; 4,951,682 and 5,000,190.

One complicating factor with the conductance catheter apparatus for measuring cardiac output is the determination of the conductivity of the patient's blood. The most common method is to draw a sample of patient's blood for making conductivity measurements in a separate measuring apparatus.

SUMMARY OF THE INVENTION

It is an object of the invention to provide a new and improved apparatus for measuring the absolute conductivity of a medium.

A further object of the invention is to provide a new and improved apparatus for measuring the absolute conductivity of blood in vivo for use in calculating cardiac output by the conductance catheter method.

Another object of the invention is to provide an apparatus for monitoring cardiac output by the conductance catheter method wherein the conductivity measurement of the patient's blood is updated periodically.

These and other objects and advantages of the invention will become apparent from the detailed description of the invention taken with the accompanying drawings.

In general terms, the invention comprises an apparatus for determining the absolute conductivity of a liquid such as human blood, and including a catheter having at least two spaced electrodes and constructed and arranged to be positioned in the ventricle of a patient's heart, means for determining the location in a ventricle of the patent's heart at which blood conductivity can be measured effectively, means for applying an electrical stimulation of known magnitude to the electrodes, means for measuring an electrical parameter between the electrodes as a result of the electrical stimulation, and means for determining the conductivity of the patient's blood from the known electrical stimulation and measured parameter. In the preferred embodiment of the invention, the electrical stimulation is a current and the measured parameter is the voltage between the electrodes.

BRIEF DESCRIPTION OF THE DRAWINGS

The single FIGURE of the drawings illustrates the preferred embodiment of the invention.

DESCRIPTION OF THE PREFERRED EMBODIMENT

The drawing shows a conductance catheter 10 positioned in a heart ventricle 12. The Catheter 10 consists of an elongate body 11 having a plurality of axially extending lumens. The body 11 is of a flexible, plastic, insulating material and may have a stiffening member extending therethrough. A plurality of band electrodes 15–24 are mounted in an equi-spaced relation on the outer surface of the body 11. The most proximal and distal electrodes which are positioned in the ventricle are driving electrodes and the intermediate electrodes are sensing electrodes. For example, if electrodes 17–24 are inside the ventricle, preferably electrodes 17 and 24 are the driving electrodes and electrodes 18–23 are sensing electrodes.

The blood conductivity determining apparatus includes an alternating, electrical stimulator 25 for providing an electrical stimulation of known magnitude. The stimulator 25 is connected by separate conductors 26 to each electrode 16–23 so that an alternating electric current or alternating voltage can be applied to each electrode or any selected pair of adjacent electrodes. The current or voltage is preferably applied at about two KHz. A measuring device 28 is connected by separate conductors 30 across each pair of adjacent electrodes 16–23 for measuring the voltage drop between each successive pairs of the electrodes if an alternating current is applied to the electrodes or a current measuring device such as an ammeter if an alternating voltage is applied. A processor 32 is coupled to the electrical stimulator 25 for receiving a signal representative of the applied current or voltage and to the measuring device 28 for receiving the voltage or current signals between each pair of adjacent electrodes 17–23 within the ventricle. The processor is programmed to select one pair of adjacent electrodes 17–23 from which conductivity may be measured. The processor is coupled to the electrical stimulator and the measuring device 28 for instructing the stimulator for energizing the driving electrodes for determining cardiac volume or the selected pair of adjacent contacts for conductivity measurements and the measuring device 28 for measuring the voltage, across or the current between the selected electrode pair. The processor is programmed to calculate blood conductivity as will be discussed more fully below. An output unit 34 is connected to the processor for displaying heart output and the blood conductivity measured between the selected pair of electrodes.

In the preferred embodiment, the stimulator 25 is an alternating current source and the measuring device is a voltmeter. In this embodiment the processor is programmed to determine absolute ventricular volume from the known constant alternating current I applied by the stimulator 25 to the drive electrodes, the voltage signals measured by the voltmeter 28 at pairs of electrodes between the drive electrodes, the known distance h between sampled electrodes and the conductivity S derived by the processor 32. Volume is determined of the blood as follows:

Volume=$Ih^2/VS$.

Volume determinations are terminated for periodic dwell periods so that the conductivity measurements can be updated periodically.

In operation, the stimulator 25 provides a constant alternating current equal to about twenty uA at two KHz to the driving electrodes, such as, 17 and 24, for example. The voltage drop between successive electrodes 17–18, 18–19, 19–20, 20–21, 21–22, 22–23, and 23–24 are then measured by the measuring device 28. The volume of each of the segments between the adjacent sensing electrodes 17–24 identified in the drawing as a, b, c, d, e and f is determined by the processor 32 using the following expression:

Volume of segments = $h^2/Kv/VS$

Where: h = the center-to-center distance between sensing electrodes;
I = the driving current applied to electrodes 15 & 16;
Kv = a constant
V = the voltage between the sensing electrodes which define the segments a–g.
S = the conductivity of the blood within the ventricle;

The volume of the ventricle 12 is the sum of the individual volumes of the segments. For a more complete description of the conductive catheter apparatus for measuring heart output and the apparatus for performing the same, reference is made to U.S. Pat. Nos. 4,898,176; 4,951,682 and 5,000,190; which are incorporated by reference herein.

The unknown quantity in the above expression is the blood conductivity S. Previously, blood conductivity was measured by drawing blood from the patient and measuring, conductivity separately in an auxiliary measuring apparatus. The present invention comprises an apparatus for measuring blood conductivity and including a processor 32 programmed for selecting a location in the ventricle at which conductivity can be measured effectively, selecting an adjacent pair of the sensing electrodes 17–24 proximal to the location and actuating the stimulator 25 which applies a constant current to these electrodes. Preferably the selected pair is the one which provide the best conductivity readings. The processor 32 may be programmed to determine an appropriate location, for example, by making a conductivity measurement between each adjacent pair of electrodes and selecting the lowest value. Alternately, the processor may be programmed to look for flat peaks in the conductivity wave form which implies field saturation and thus a good reading. The voltage drop between the selected pair of electrodes is then measured by measuring device 28. The ratio of the applied current to the measured voltage bears a constant ratio to the true conductivity of the blood. This constant calibration ratio must be determined by the processor 32 for each specific electrode dimension and spacing and can be established by using a standard liquid of known conductivity or by computer simulation. The calibration ratio remains substantially constant as long as the electrodes are close to each other and there is a sufficient volume of blood surrounding the electrodes. Once the calibration ratio for each particular electrode dimension has been established, the true conductivity s of the blood can be determined from the following expression:

S = IKc/V

Where: I = the applied current
Kc = the calibration ratio
V = the measured potential If a two point current source is positioned at a unit distance apart in an infinite volume of material with uniform conductivity and the constant current injected by the source is I and the potential drop across the source is V, then it can be mathematically shown that the ratio I/V is the true conductivity of the material divided by 3.14. As a result, by multiplying the ratio I/V by 3.14 (the calibration ratio), the true conductivity of the material can be determined.

For different electrode geometry, the calibration ratio will differ from 3.14. Computer simulations and experimental evidence has shown that there is no appreciable change in the calibration ratio as long as the electrode dimensions and the material volume around the electrodes is of the order of three times or more than the electrode spacing. It has also been found that the calibration ratio is predominantly dependent on the size of the electrode rather than electrode spacing.

A typical conductance catheter has electrodes spaced about 10 mm from edge to edge. The electrodes may be about 2.5 mm in both length and diameter and may be formed of any suitable material, such as, stainless steel or an alloy of 90% platinum and 10% iridium. The catheter body is an extruded plastic material having a plurality of lumens. A plastic stiffening member is preferably disposed in one of the lumens and the conductors from the electrodes 15–24 are disposed in a different lumen.

Because the blood conductivity of a patient may change during surgery as a result of fluids which may be administered, it is desirable to update the conductivity parameter from time to time in order for the patient's cardiac output to be determined accurately. Therefore, the cardiac output monitoring may be interrupted for a short dwell period each few heartbeats by the processor 32 and the conductivity measurement is updated for use when the cardiac output monitoring resumes at the end of the dwell period. Alternatively, the cardiac output and conductivity measurements can be done simultaneously by employing multiplexing techniques.

While the invention is illustrated and described in relation to a catheter having ten electrodes, blood conductivity can be determined with catheters having two or any number greater than two consistent with the requisite spacing.

Although only a single embodiment of the invention has been illustrated and described, it is not intended to be limited thereby, but only by the scope of the appended claims.

We claim:

1. An apparatus for determining the absolute conductivity of blood, said an apparatus including a catheter comprising an elongate body having a distal end and a proximal end and a plurality of electrodes on the outer surface thereof and spaced apart between the proximal and distal ends, one of said electrodes being positioned adjacent to the distal end and being the distal electrode and a second electrode being disposed adjacent the proximal end and being the proximal electrode, there being a plurality of measuring electrodes disposed between the distal and proximal electrodes, means coupled to the measuring electrodes for determining the location within a patient's ventricle where conductivity readings can optimally be obtained when the measuring electrodes are positioned in the ventricle, whereby the catheter may be positioned so that a pair of adjacent ones of the measuring electrodes are proximal to the location, means for applying an alternating electric current of known magnitude to the pair of adjacent measuring electrodes, means for measuring the voltage between the pair of adjacent measuring electrodes and means for determining the absolute conductivity of blood in the ventricle from the alternating electric current and the measured voltage.

2. The apparatus set forth in claim 1 wherein the means for determining comprises a processor programmed to determine blood conductivity S from the expression:

$$S = IKc/V$$

Where: I=the applied current
Kc=a constant
V=the measured voltage.

3. The apparatus set forth in claim 2 wherein there are a plurality of electrodes on said catheter, said electrodes having known spacing.

4. The apparatus set forth in claim 2 wherein said catheter includes a plurality of electrodes greater in number than two, said processor being programmed for determining which adjacent pair of electrodes of said plurality are located in the patient's ventricle at the optimal position where a conductivity measurement can be obtained, said current applying means being operative to energize the pair of electrodes at the position, said voltage measuring means being operative to measure the voltage between the pair of electrodes at the location.

5. Apparatus for determining cardiac volume including a catheter constructed and arranged to be positioned in a ventricle of a patient's heart, the catheter comprising an elongate body having a proximal end and a distal end within the ventricle and a plurality of spaced electrodes on the outer surface thereof and between the proximal and distal ends, said electrodes being spaced a predetermined distance from each other, means for providing a constant alternating electric current to the distal and proximal electrodes, means for measuring the voltage between pairs of adjacent electrodes located between the distal and proximal electrodes and resulting from said electrical current, processor means for determining cardiac volume using an expression in which the absolute conductivity of the patient's blood is a variable, said processor being programmed (1) to determine the location of a position in the ventricle in which conductivity measurements can optimally be made, (2) to actuate the electrical current means for applying a constant electrical current of known magnitude to a selected pair of adjacent electrodes proximal to the located position, (3) to measure the voltage between the selected pair of adjacent electrodes, and 4 to determine the absolute conductivity of the patient's blood from the known electrical current and the measured voltage.

6. The apparatus set forth in claim 5 wherein said processor is further programmed to (1) periodically terminate the cardiac volume determination for a dwell period; (2) to determine the absolute conductivity of the patient's blood during each dwell period, and to resume the cardiac output determination at the end of the dwell period using the blood conductivity determined during the preceding dwell period.

7. The apparatus set forth in claim 5 wherein said processor is further programmed to simultaneously determine cardiac output and blood conductivity.

* * * * *